United States Patent [19]

Aslesen et al.

[11] Patent Number: 4,689,989

[45] Date of Patent: Sep. 1, 1987

[54] METHOD AND APPARATUS FOR TESTING THE OUTFLOW FROM HYDROCARBON WELLS ON SITE

[75] Inventors: Kerby S. Aslesen, Vernal, Utah; John R. Bocek; Dennis R. Canfield, both of Casper, Wyo.; Ke-Tien Liu, Sugar Land, Tex.

[73] Assignee: Chevron Research Company, San Francisco, Calif.

[21] Appl. No.: 747,706

[22] Filed: Jun. 24, 1985

[51] Int. Cl.$^4$ .............................................. G01F 5/00
[52] U.S. Cl. .............................. 73/61.1 R; 73/861.04
[58] Field of Search ............ 73/61.1 R, 32 R, 861.04; 364/502, 510, 550

[56] References Cited

U.S. PATENT DOCUMENTS

| | | | |
|---|---|---|---|
| 3,304,766 | 2/1967 | Hubby | 73/61.1 R |
| 3,488,996 | 1/1970 | Pfrehm | 73/61.1 R |
| 3,673,574 | 6/1972 | Holm | 364/510 |
| 3,892,127 | 7/1975 | Cirulis et al. | 73/61.1 R |
| 3,906,198 | 9/1975 | November | 73/61.1 R |
| 3,964,037 | 6/1976 | Lamphere | 73/32 R |
| 4,010,645 | 3/1977 | Herzl | 73/32 R |
| 4,048,854 | 9/1977 | Herzl | 73/61.1 R |
| 4,059,744 | 11/1977 | Elderton | 73/61.1 R |
| 4,127,028 | 11/1978 | Cox et al. | 73/194 B |
| 4,187,721 | 12/1980 | Smith | 73/194 B |
| 4,215,567 | 8/1980 | Vleck | 73/61.1 R |
| 4,311,054 | 1/1982 | Cox et al. | 73/861.38 |
| 4,340,938 | 7/1982 | Rosso | 73/61.1 R |
| 4,422,338 | 12/1983 | Smith | 73/861.38 |
| 4,441,361 | 4/1984 | Carlson et al. | 73/861.04 |

OTHER PUBLICATIONS

Sales brochure, Micro Motion, Inc.—generally describes the Coriolis-based mass measurement device.
Plache, K. O., "Coriolis/Gyroscopic Flow Meter", Mechanical Engineering, Mar. 1979, pp. 36 et seq.
Micro Motion, Inc. "Mass Flow Meter Remote Electronics Instruction Manual"—describes the Coriolis-based device in detail.

Primary Examiner—Stewart J. Levy
Assistant Examiner—Hezron E. Williams
Attorney, Agent, or Firm—S. R. LaPaglia; E. J. Keeling; V. A. Norviel

[57] ABSTRACT

A portable instrument for testing at the wellhead continuously, or a stationary instrument for use at a production battery, the outflow of crude hydrocarbons from the well or wells. The invention utilizes a simple relationship of density and thermal coefficients of expansion of the oil and the water, together with improved instrumentation to measure mass flow rate of the crude mixture, to produce accurate continuous readings of oil and water contents in the crude. The invention depends upon state of the art technology both as to the crude handling and the electronics portions of its apparatus.

32 Claims, 2 Drawing Figures

METHOD AND APPARATUS FOR TESTING THE OUTFLOW FROM HYDROCARBON WELLS ON SITE

FIELD OF THE INVENTION

The present invention pertains to a stationary or portable instrument for testing, on site at the wellhead or at the production tank battery, the output of crude hydrocarbons from a well. More in particular, the invention provides method and apparatus to continuously measure the amounts of crude oil and of water in the oil and water mixture outflow from the well.

BACKGROUND OF THE INVENTION

Knowing the amounts of oil and water in the produced fluid outflow from hydrocarbon wells is of great commercial importance in today's petroleum industry. Problems arise in that crude oil contains many impurities such as gas in solution and paraffin, can be a very thick molasses-like material, contains sand and water, and presents many other obstacles to accurate testing of the oil and water contents. Errors in the range of 10% to even as high as 200% in determining the amount of oil in well production fluid or crude oil have been known to occur using conventional testing equipment and methods.

Because of the nature of crude oil and all of the impurities therein, it is not always possible to use ordinary orifice meters, turbine meters and the like. Conventional systems involve heating of the crude oil to dissolve any paraffin, since paraffin deposits will be detrimental to the equipment. Further, the heating aids in releasing dissolved gases which can produce inaccuracies in the results. Thereafter, the heated and thus degassed oil is separated and the water, sand and other foreign materials are removed. The oil remaining is passed on through conventional meters to measure the quantity of oil A gravity type separation, usually involving a weir, performs the actual oil/water separation.

Most crude oils contain both dissolved and free gas. The presence of this gas above certain percentages is a problem in producing accurate data according to the invention. It is for this reason necessary that, before the well fluids are measured for density and for mass, the free gas be removed. In the odd situation where a well produces fluids having no free gas, it is in that case possible to pass the produced well fluid directly into the invention apparatus.

Crude oil is produced together with varying amounts of water, and, in fact, the water can vary from zero to 99% of the total outflow of the well. This water can be in the form of free water or can be in the form of an emulsion together with the hydrocarbons. Still further, the emulsion can contain the water rather loosely combined with the hydrocarbon materials or rather intimately combined. In fact, it is possible that the combination of the water and crude oil can be so "tightly" emulsified that it is extremely difficult to separate the emulsion.

The prior art utilizes a system dependent upon a complex "plumbing" arrangement wherein a group of wells feed into a common production tank battery. The complex piping arrangement permits any one well feeding this battery to be in effect segregated out and have its output fed to a testing means. Tight emulsions in particular are a problem for conventional well testing. Further, in certain situations, exceedingly expensive equipment including heaters and the like are needed in order to adequately test all of the wells feeding into the common battery. The presence of paraffin in the hydrocarbon outflow creates additional problems, fouling of valves and meters, difficulty of measuring oil content, and the like.

Yet another problem resides in the presence of dissolved (solution) gas in the crude outflow from the well. This solution gas can evolve from the crude at any time during the process, and this random factor has a severe detrimental effect on the accuracy of conventional systems. A pressure drop anywhere in the conventional technique will, of course, cause an evolution of the gas.

Dependent upon the particular well and the crude oil and gas it produces, separation sometimes requires three phase and sometimes two phase separation. The invention can operate with both.

The invention also permits downsizing of the equipment used which is an advantage in producing a portable device, i.e., an apparatus embodying the invention which can be mounted on a simple pick-up truck to be brought out to the wellhead and used directly at the well. This portability occurs because it is often relatively easy to separate gas from well fluids, but relatively more time consuming to break apart the well fluids into the different components. Since the invention can work on gas free liquid whatever liquid components are contained therein, this permits the downsizing and the advantage of portability.

The term "free gas" as used herein shall be understood to mean any substance which is or will be in a gaseous state at the time it passes through the invention apparatus.

Knowing the amounts of oil and water in the produced fluid outflow from hydrocarbon wells is of great commercial importance in today's petroleum industry. In the conventional capacitance probe method of measurement, the accuracy of measurement for the amounts of oil and water deteriorates as the amount of water increases, especially at water contents above the 25-30% range. The use of ordinary orifice meters, turbine meters and the like is not desired because the meters, per se, are not too accurate and because the meters, especially the turbine meters, tend to require a lot of maintenance.

Usually, production well fluids are free of solids such as sand and have a pour point which is below the temperature at which the amounts of the oil and water are being measured. If solids are present, such as sand, then means must be provided to remove the sand before measurements are made to determine the oil and water content of the fluids. This is true for prior art devices and is also true for the use of the apparatus of this invention in order to obtain an accurate density signal. Further, high pour point crudes tend to plate paraffin out on any measuring device and this impairs the accuracy and efficiency of such devices. Conventional systems involve heating of the crude oil to a temperature above its pour point to prevent the deposition of paraffins in the measuring apparatus. Such a heating step would also be required using the method and apparatus of this invention in order to obtain an accurate density signal.

The prior art includes methods and apparatus that pass the sample mixture through a flow meter and an indirect density measuring device in series. This data can be processed to produce water and oil readings in volume units. However, the results are less accurate than those produced by the invention. The primary differences which are thought to produce these advantages include that the invention uses a mass measuring device in place of a flow meter, and that the same element (a vibrating tube) is used in the invention to measure mass and density, as compared to two separate means to do so in each prior art devices.

The prior art includes many devices which unsuccessfully attempt to solve the problems solved by the present invention. The ITT Barton Model 1200 device is said to determine the percentage of oil and water in a two-component fluid under flowing line conditions. The computer displays total oil and total water on two separate totalizers, plus total fluid flow rate indication. The percentages of oil and water are determined by measuring the flowing specific gravity of the fluid using a specially designed "ratio tube" and associated electronics. Liquid flow rate is measured using a turbine meter or positive displacement meter.

Testing has shown that the results using the ITT Barton device are not as accurate as the results using the device of this invention.

The present invention solves all of the above problems, and provides a measuring device which produces very highly accurate results.

SUMMARY AND ADVANTAGES OF THE INVENTION

In its most general application, the invention can be applied to determining the amounts of two liquids having different densities of said liquids. It can be applied, for example, to determine the amount of alcohol and water in beer or wine, the amounts of oil and water as in the environment for which the invention was developed, and in other environments which will present themselves to those skilled in the various arts in which the invention can be used. Oil field usage of the apparatus of this invention requires that the density measurements be corrected to a density at a reference temperature because of the variations in the field temperatures at which the density of the oil is actually measured. This correction of density allows for the use of a standardized correlation of density versus the percentage fraction of the components in the mixture. However, for example, in a brewery or a winery where the entire system is at one temperature, no such temperature correction for density is necessary, since a standardized single temperature correlatory of density versus percent fraction of the components in the mixture can be used. Thus, the invention broadly does not require this temperature correction facet even though it is needed for the particular oil field environment for which the invention was developed.

The invention depends upon the use of recently developed improved equipment which has the ability to accurately measure the mass flow rate of the crude oil, its temperature (optionally), and its density at the wellhead. This equipment is small, and highly reliable in use. Density is derived from a secondary signal in the mass flow meter using a density processor.

The invention apparatus as applied to oil field usage corrects the density measurement to a reference temperature, which is usually 60° F. This facet of the invention is important because it is necessary to know at what temperature the oil/water "cut" was made. That is, as explained in further detail below, the invention makes a mathematical analysis of the oil and water fractions, and it is necessary to know the temperature at which this was done, i.e., what were the densities of the water and of the oil at the time this was done. The invention apparatus automatically accommodates correction to this reference temperature.

The invention provides a combination of software and other facets to produce a portable or stationary, highly reliable, simple electronic device to produce a continuous output to a very high degree of accuracy of the amounts of oil and water in the production fluid.

An important advantage of the invention is that it virtually entirely uses proven state of the art oil handling equipment as well as proven electronic components. The invention method takes the form of the programming of a set of equations to produce the advantageous continuous accurate oil and water outputs in volume terms.

The invention depends upon very simple engineering principles applied in a unique manner. More in particular, the invention utilized the fact that one can, using the outputs of the new improved measuring meters, in effect "back engineer", from known quantities of the density and mass flow of the crude oil, and utilizing text book known quantities for the densities of water-free oil and of water, and then performing some relatively simple calculations and making temperature corrections, to then produce accurate output readings of the amounts of oil and water corrected for temperature of the crude oil to a reference temperature.

Crude oil can contain various amounts of non-liquid materials such as gas and solids, e.g., sand and wax. The accuracy of the results of the measurements using the apparatus and method of this invention can be improved by the preferred prior removal of the gaseous and solid materials or, in the case of waxy materials, in heating the crude oil to, in effect, dissolve the wax into the liquid hydrocarbon oil. By "liquid" in this application is meant liquid under the conditions at which the fluid or mixture is being tested. Further, because of the use of modern electronics and computing power, the invention produces optional output signals which can be used in automated processes, for safety shut-offs, and the like.

In conjunction with the use of modern electronics and computer power as described herein, the invention also provides means to automatically alert the operator of the possibility of there being free gas going through the invention device. This is done by programming into the apparatus values anticipated for the particular oil being measured. That is, if the density of the mixture is less than the minimum anticipated value, then that is a strong indication that there may be excessive free gas in the mixture. This free gas must be removed or corrected for or erroneous readings will result.

SIMPLIFIED EXPLANATION OF THE METHOD OF OPERATION OF THE INVENTION

Figure 2:
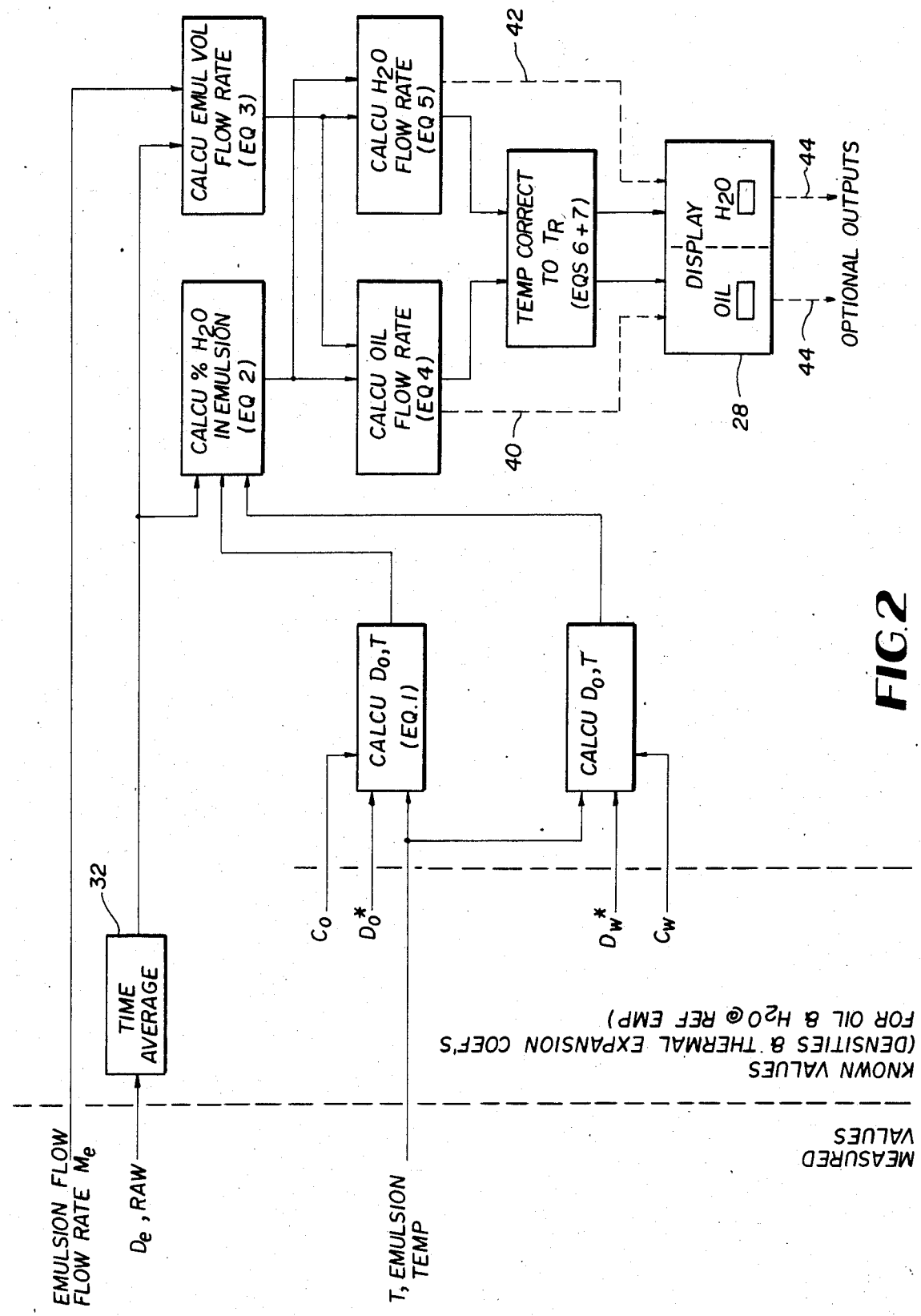
FIG. 2 is a detailed logic diagram showing the manner in which the invention operates.

The following two subsections under this main heading will be useful in aiding understanding of the the method of the invention, and will aid in understanding FIG. 2, the approach of the invention as applied in actual practice.

Standard Mixture Density Calculation

In the usual situation, the mixture density is sought, and the details of the components are known.

Given:
quantity of component X e.g. = 60 volume units
quantity of component Y e.g. = 40 volume units
density of component X($D_x$) e.g. = 0.8 weight/volume units
density of component Y($D_y$) e.g. = 0.4 weight/volume units
Find:
density of mixture ($D_{mix}$)

$$D_{mix} = \frac{D_xX + D_yY}{X + Y} = \frac{.8(60) + .4(40)}{60 + 40} = .64$$

Invention Method-Example Calculation

This example uses the same numbers and values used above.

The invention method has available to it (corresponding to "givens"), by measurement, as known quantities, and by calculation; $D_{mix}$ (which is the crude oil/water emulsion density as measured), $D_x$ (which is the known water density), $D_y$ (which is crude oil density as measured), and total flow; X plus Y (which is total volume flow).

The invention makes numerous volume and temperature corrections, set forth in greater detail below:

The invention seeks to determine (find) X and Y, the water and oil quantities.

Working the above example, in effect backwards $$X + Y = 100 \text{ (total volume flow)}$$

$$D_{mix} = \frac{D_xX + D_yY}{X + Y} \quad X = 100 - Y$$

$$.64 = \frac{.8(100 - Y) + .4(Y)}{100} \quad 64 = 80 - .8Y + .4Y$$

$$.4Y = 16$$

$$Y = 40$$

$$X = 60 \text{ (checks)}$$

DETAILED DESCRIPTION OF THE PREFERRED EMBODIMENT

Figure 1:
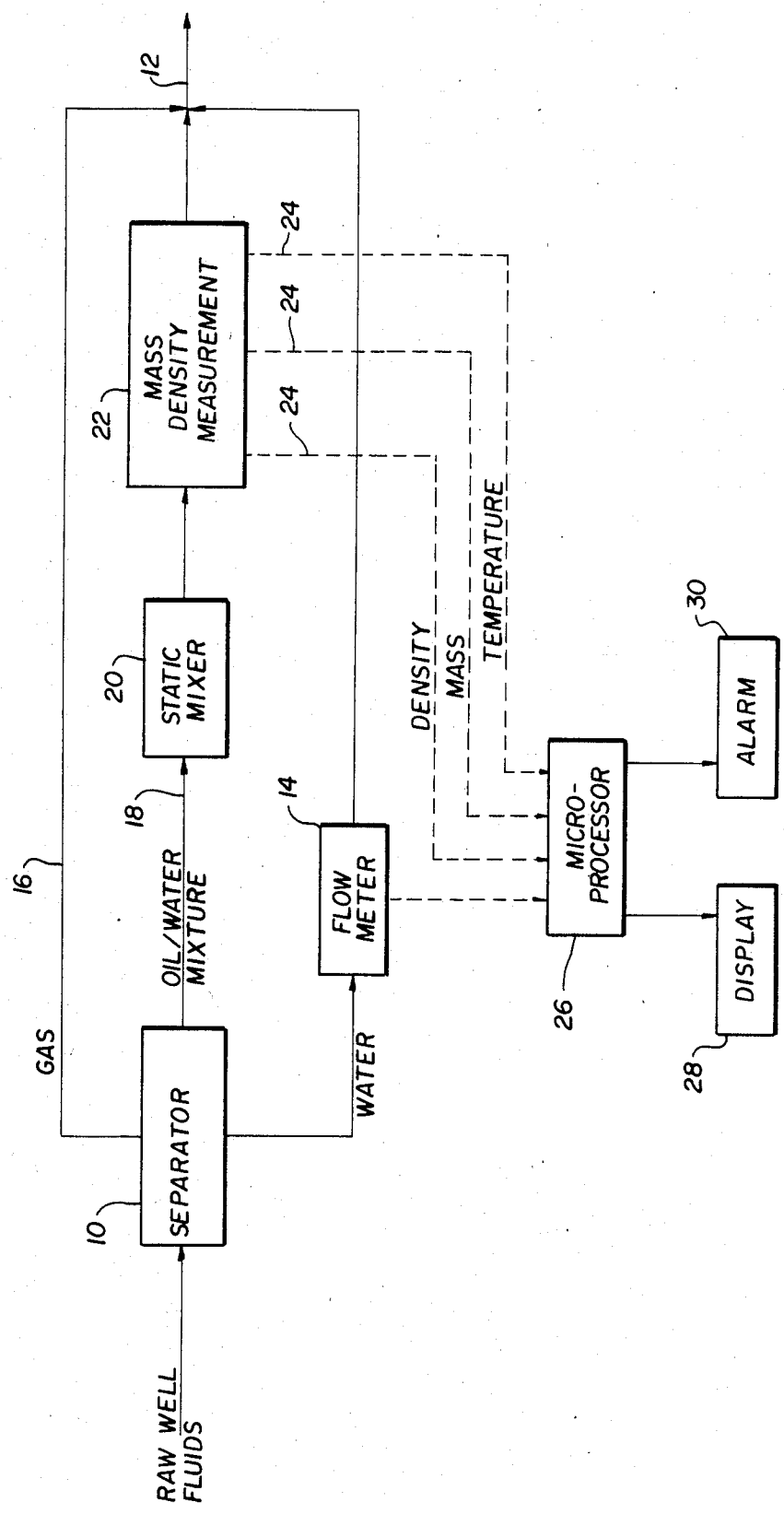
FIG. 1 is a schematic diagram showing the invention overall including the crude oil handling portion and the electronics portion.

Referring now to FIG. 1, there is shown a schematic diagram, with many parts removed, of a preferred embodiment of the invention, both as to its fluid handling portions and the electronic portions which handle the data and produce the continuous readings of oil and water volume output from the well.

Reference numeral 10 indicates a separator conventionally used in petroleum operations to separate hydrocarbon liquids such as gas condensate, oil, and the like from water, and from any gas present in the produced fluids. Such separators can be either two-phase or three-phase. Two-phase separators separate only gas and liquid, the liquid often being oil and water as an emulsion. Three-phase separators in addition separate free water. Both types of devices are well known and well developed, they can be either horizontal or vertical, and many different varieties are available. The invention can operate with all such separators.

For the sake of example, a three-phase separator is shown wherein a gas fraction, an oil/water mixture fraction and a water fraction are produced. The three fractions are recombined into a line 12. The invention can be used in a conventional production tank battery serving a plurality of wells. Such batteries and their piping arrangements are well known. Basically, they provide that the production from many wells are manifolded together, while at the same time the production of each well can be individually directed to test apparatus, such as the present invention, to perform various functions on the output, such as, as is the case in the present invention, determining the amounts of hydrocarbon liquids and of water in the produced fluids. The water fraction from the bottom of the separator is directed to a flow meter 14 where it is measured and then combined into line 12.

The gas fraction can be directed through a line 16 directly to the output line 12, or can be flared or can be subjected to gas processing and then sold. Various meters and the like can optionally be used in line 16 if desired, as is well known to those skilled in the art. In the event a two-phase separator is used, then meter 14 and its line will be omitted.

The oil/water mixture of interest, which can be a mixture of water and an oil/water emulsion, or various combinations thereof, is directed in a line 18 to a static mixer 20 which in effect homogenizes the oil/water mixture in order improve the final output test results. This static mixer 20 is optional and may or may not be needed, depending on the particular usage.

After mixer 20, the oil/water mixture passes on through an instrument 22 which measures its density, its mass, and its temperature, and passes on this data through a set of lines 24 to a microprocessor 26.

The meter 22 can be any suitable device which will produce the density, mass flow and temperature data required by the remaining portions of the invention as described below. By "mass flow" data is meant a raw signal which can be represented either by total mass over a discrete period of time (a pulse signal) or a mass flow rate (an analog signal). In the testing that has been done to date, mass/density meters operating on the Coriolis principle have been found to be particularly advantageous. More in particular, a commercial device sold by Micro Motion of Boulder, Colo., and in particular their model D meter equipped with model DT7 liquid densitometer has been found to be particularly advantageous.

This particular Micro Motion model D meter produces two outputs, an analog signal and a frequency or pulse signal, both of which correlate to the total mass flow through the meter. The invention can operate with either of these two signals produced by this model D meter.

The above is a highly simplified explanation of the fluid handling part of the present invention's apparatus. As will be clear to those skilled in the art, many valves, meters, and other components have been omitted for the sake of clarity.

The microprocessor 26 can be of any conventional sort, and is simply programmed to accommodate the logic set forth in FIG. 2 and described below in regard to the particular equations which are operated upon as shown in FIG. 2.

The output of the microprocessor 26 is directed to a display means 28, again described in greater detail below in regard to FIG. 2, and also to alarm means 30.

The alarm or alerting means 30 are a substantial step forward of the present invention in this art.

An important problem with which the invention deals and with which the alarm means 30 are concerned is the presence of free gas in the hydrocarbon liquids. Such gas will cause a reduction in density and at the same time will have a severe detrimental effect on the accuracy of the results produced by the invention. The alarm means 30 can be programmed into the microprocessor 26 so that it will alert the operator to such a reduction of the density below the lowest density anticipated to be encountered by the fluids being tested, e.g., the mixture of oil and water, an emulsion of oil and water or the individual components. As noted above, such a lowering of density will be an indication of the presence of free gas in the liquids.

The particular meter with which the invention operates is relatively sensitive to free gas in the crude oil. It is necessary that this free gas be removed in order to get the accurate results to which the present invention is directed. Accordingly, one of the primary purposes of the separator 10 is to remove the gas from the crude before the emulsion passes on through the line 18 to the measuring means 22. Following this logic further, in the event a well having virtually no free gas in its crude were to be encountered, it would be possible to eliminate the separator 10 and direct the raw well fluids directly into the remaining parts of the circuitry shown in FIG. 1. More specifically, the free gas needs to be removed because, due to the particular meter with which the successfully constructed embodiment of the invention has been built, the density data is adversely effected as to accuracy, even though, interestingly enough, the mass flow data is relatively unaffected.

Extensive testing has been done to improve the improvement wrought by the present invention over the prior art.

The following Table 1 summarized a number of tests which were run based on standard specimens. Two different kinds of standard separators were used, and three standard prior art devices were compared against the invention device. All tests were run under the same conditions to assure the accuracy of the comparison results set forth in the following Table 1.

TABLE 1

| Standard Specimens (% water) | Separator Type | Measured % of Water | | | |
|---|---|---|---|---|---|
| | | Standard Devices | | | Invention Device |
| | | A | B | C | |
| 0 | 3-phase | 1.7 | 0 | 0.3 | 0 |
| 25 | 3-phase | 30.3 | 32.6 | 74.2 | 24.6 |
| 70 | 2-phase | 84.2 | 87.3 | 82.3 | 71.1 |
| 90 | 2-phase | 97.3 | 98.3 | 100.0 | 88.8 |

As is clear, the present invention produced consistently more accurate results than any of the prior art standard devices, and further it can be seen that the error of the present invention was sometimes below and sometimes above the standard specimen correct water percentage. The standard devices, on the other hand, consistently read overly high as to percent water, which means a correspondingly consistent low reading as to the percent oil. The data produced by test equipment such as the standard equipment of this table and the invention device is very important, and thus inaccurate data is highly undesirable. Such inaccurate data can have legal implications in regard to royalty payments for oil produced, and, perhaps more importantly, can be the basis on which reservoir engineers can make faulty decisions because of inaccurate data.

Referring now to FIG. 2, there is shown a logic flow diagram of the manner in which the electronic portions of the invention utilize the data produced by the meter 22 of FIG. 1 in order to produce the continuous readings of oil and water percents in the crude oil under test.

The block 32 marked "TIME AVERAGE", time averages the raw emulsion density data in order to produce more accurate results. This time averaging function can be done either directly in the hardware in the computing means 26, or else can be done in the software. Testing has shown that the accuracy of the final results are greatly improved when this time averaging is performed. The need for the time average is believed to be due to the inherent nature of the densitometer.

Most of the individual blocks shown in FIG. 2 perform a particular calculation, and the designation "EQ." followed by a number is the key to the following explanation wherein each of those equations (EQ.) is explained in greater detail.

An asterisk superscripted over a parameter indicates that the parameter gives the value at the reference temperature $T_r$. Subscripts "o" and "w" stand for oil and water, respectively.

A. Known Parameters

For a given production well, the densities of "pure oil" and "pure water" are constant and can be considered given for the calculations. In addition, of course, their thermal expansion coefficients are known.

$D_o^*$: density (lb/BBL) of oil at reference temperature $T_r$.

$D_w^*$: density (lb/BBL) of water at reference temperature $T_r$.

$C_o$: thermal expansion coefficient (lb/BBL/°F) for oil.

$C_w$: thermal expansion coefficient (lb/BBL/°F) for water.

$T_r$: reference temperature (conventionally chosen as 60° F.).

B. Measurements by Meter 22

Three quantities are provided by meter 22:

$D_e$: density (lb/BBL) of oil/water emulsion at measurement temperature T.

$M_e$: mass flow rate (lb/min) of oil/water emulsion.

T: temperature (°F.) of oil/water emulsion at the meter.

C. Computation Procedure

1. Compute densities of oil and water at temperature T.

$$D_{o,T} = D_o^* - C_o(T - T_r) \qquad \text{EQ. 1}$$

$$D_{w,T} = D_w^* - C_w(T - T_r)$$

where $D_{o,T}$ and $D_{w,T}$ are the densities of oil and water at temperature T.

EQUATION 1 is exemplative only. Other equations well known to those skilled in the art, such as those developed by API (American Petroleum Institute) can also be used.

2. Compute the fraction of water in the oil/water emulsion.

$$X_w = \frac{D_e - D_{o,T}}{D_{w,T} - D_{o,T}} \qquad \text{EQ. 2}$$

3. Compute volumetric flow rate of the oil/water emulsion.

$$Q_c = \frac{M_c}{D_c} \text{ bbb/min.} \quad \text{EQ. 3}$$

4. Compute volumetric flow rate of oil at temperature T.

$$Q_o = Q_c(1 - X_w) \text{ BBL/min.} \quad \text{EQ. 4}$$

5. Compute volumetric flow rate of water at temperature T.

$$Q_w = Q_c X_w \text{ BBL/min.} \quad \text{EQ. 5}$$

6. Compute volumetric flow rate of oil at reference temperature.

$$Q_o^* = \frac{Q_o D_{o,T}}{D_o^*} \text{ BBL/min.} \quad \text{EQ. 6}$$

7. Compute volumetric flow rate of water at reference temperature.

$$Q_w^* = \frac{Q_w D_{w,T}}{D_w^*} \text{ BBL/min.} \quad \text{EQ. 7}$$

8. Integrate the instantaneous flow rates of oil and water computed from EQUATIONS 6 and 7 with respect to time to obtain cumulative total amounts of oil and water within the time interval of interest.

$$V_o^* = \Sigma Q_o^* \Delta t \quad \text{EQ. 8}$$
$$V_w^* = \Sigma Q_w^* \Delta t$$

Where $\Delta t$ denotes an arbitrary time interval during which the measurements of raw data are taken.

A separate logic block to perform this summation (EQ. 8) is not specifically shown in the drawings, as such means could be included in the display 28 or elsewhere in the circuitry. In any event it is a simple matter to perform such an accumulation of data.

D. Example Computation
Given:

| $D_o^*$ = 0.8315 | g/cc = 291.4 | lbs/BBL |
| $D_w^*$ = 1.0328 | g/cc = 362.0 | lbs/BBL |
| $C_o$ = 0.000490 | g/cc/°F. = 0.17175 | lbs/BBL/°F. |
| $C_w$ = 0.0001725 | g/cc/°F. = 0.06046 | lbs/BBL/°F. |
| $T_r$ = 60° F. | | |

Measured:

$D_e$ = 0.9546 g/cc = 334.6 lbs/BBL $T$ = 95° F.

$M_e$ = 140.0 lb/min.

Computations:
1. Density of pure oil at 95° F. (EQUATION 1)

$$D_{o,T} = D_o^* - C_o(T - T_r)$$
$$= 291.4 - 0.17175 (95 - 60)$$
$$= 285.4 \text{ lb/BBL}$$

Density of pure water at 95° F. (EQUATION 1)

$$D_{w,T} = D_w^* - C_w^*(T - T_r)$$

$$= 362.0 - 0.06046 (95 - 60)$$

$$D_{w,T} = 359.9 \text{ lb/BBL}$$

2. Water content in emulsion (EQUATION 2)

$$X_w = \frac{D_e - D_{o,T}}{D_{w,T} - D_{o,T}}$$

$$= \frac{334.6 - 285.4}{359.9 - 285.4}$$

$$= 0.66$$

3. Volumetric flow rate of emulsion (EQUATION 3)

$$Q_c = \frac{M_c}{D_c} = \frac{140.0}{334.6} = 0.418 \text{ BBL/min.}$$

4. Volumetric flow rate of oil (EQUATION 4)

$$Q_o = Q_c(1 - X_w)$$

$$= 0.418 \times (1 - 0.66) = 0.142 \text{ BBL/min.}$$

5. Volumetric flow rate of water (EQUATION 5)

$$Q_w = Q_c \cdot X_w$$

$$= 0.418 \times 0.66 = 0.276 \text{ BBL/min.}$$

6. Volumetric flow rate of oil at 60° F. (EQUATION 6)

$$Q_o^* = Q_o \cdot \frac{D_{o,T}}{D_o^*}$$

$$= 0.142 \times \frac{285.4}{291.4}$$

$$= 0.142 \times 0.9794 = 0.139 \text{ BBL/min.}$$

7. Volumetric flow rate of water at 60° F. (EQUATION 7)

$$Q_w^* = Q_w \cdot \frac{D_{w,T}}{D_w^*}$$

$$= 0.276 \times \frac{359.9}{362.0}$$

$$= 0.276 \times 0.994 = 0.274 \text{ BBL/min.}$$

8. Cumulative total amounts of oil and water during a one-hour period at constant oil and water flow rates (EQUATION 8)

$$V_o^* = \Sigma Q_o^* \Delta t$$

$$= (0.139 \text{ BBL/min.}) \times (60 \text{ min.})$$

$$= 8.34 \text{ BBL of oil}$$

$$V_w^* = \Sigma Q_w^* \Delta t$$

$$= (0.274 \text{ BBL/min.}) \times (60 \text{ min.})$$

$$= 16.44 \text{ BBL of water}$$

As is clear to those skilled in the art, the power of the computing means 26 and the display 28 of FIG. 2 permits picking up the output of any of these various Equations from the various blocks shown in FIG. 2 and feeding them directly to the display 28. The dotted lines 40 and 42 in FIG. 2 from the blocks which calculate Equations 4 and 5, respectively, feeding directly into the display means 28 are an indication that the display means can also be used to display oil and water data not corrected for temperature. Such uncorrected data may be of interest for various different reasons known to those skilled in the art.

The lines 44 exiting from the display means 28 marked "optional outputs", are an indication that the results produced by the invention can be used to drive other apparatuses, and in other environments, external of the invention apparatus. For example, it would be a simple matter to rearrange Equation 2 so as to produce on these optional output lines 44 data corresponding to the weight content rather than the volume contents of the oil and the water being measured. Such signals can be used to operate other processes or other devices. Many other such examples will present themselves to those skilled in these arts.

While the invention has been described in detail above, it is to be understood that this detailed description is by way of example only, and the protection granted is to be limited only within the spirit of the invention and the scope of the following claims.

What is claimed is:

1. A method of determining the amounts of a first and of a second component in a flowing mixture comprising said first and second components, said first and second components being liquids and having different densities, comprising the steps of (i) measuring the mass flow of said mixture, (ii) determining the density of said mixture with a mass density meter operating on the Coriolis principle, said mass density meter using a common element to measure mass flow and density, (iii) obtaining values for the densities of said first and second components; (iv) calculating the amounts of said first and second components in said mixture based on said measured mixture mass flow rate, measured mixture density, and said first and second component obtained values for their said densities; and (v) displaying the calculated amounts of said first and second components in said mixture.

2. The method of claim 1, and the steps of measuring the temperature of said mixture, obtaining values for the thermal coefficients of expansion of said first and of said second components, and performing said calculating amounts step to include said measured mixture temperature and said thermal coefficients values to correct the amounts displayed in said displaying amounts step for the difference in temperature between the measured temperature of said mixture and a predetermined reference temperature.

3. The method of claim 1, wherein the method determines the volume amounts of said first and second components.

4. The method of claim 1, wherein said mixture is produced fluid from a well, said first component is liquid hydrocarbons, and said second component is water.

5. The method of claim 4, and the step of performing the method using a portable apparatus at the wellhead of a hydrocarbon well.

6. The method of claim 4, and the step of performing the method using a stationary apparatus.

7. The method of claim 4, and the step of removing gas present in said produced well fluid prior to said first step of measuring mass flow rate.

8. The method of claim 4, and performing the method at a production tank battery serving a plurality of said wells.

9. The method of claim 8 which includes the step of first removing gas from said produced well fluid prior to said step of measuring mass flow.

10. The method of claim 2, wherein said calculating step includes the substeps of first calculating the density of said first and second components at said measured temperature and utilizing said measured temperature and said values for the densities and the thermal coefficients of expansion of said first and second components, then the substep of calculating the percent of one of said first and second components in said mixture utilizing the measured mixture density and the previously calculated values for the densities of said first and second components, calculating the volume flow rate of the mixture utilizing said measured value of mixture mass flow and mixture density, the substeps of calculating flow rates of said first and of said second components utilizing the output of said last mentioned substeps of calculating the percent content of one of said components in said mixture, and the substep of calculating the mixture volume flow rate, and then the substep of temperature correcting the outputs of said last mention two substeps of calculating the first and second component flow rates.

11. The method of claim 10, wherein said mixture is produced fluid from a well, said first component is liquid hydrocarbons, said second component is water, and the step of time averaging the measured value of the density of said mixture.

12. The method of claim 1, and operating alerting means in the event the measured mixture density falls below the smallest value of said obtained values for the densities of said first and second components.

13. Apparatus for determining the amounts of a first and of a second component in a flowing mixture comprising said first and second components, said first and second components being normally liquids and having different densities; means to flow said mixture through said apparatus, means to measure the mass flow, the density, with a mass density meter operating on the coriolis principle, said mass density meter using a common element to measure mass flow and density and the temperature of said mixture; means to obtain values for the densities of said first and of said second components, means to calculate the amounts of said first and second components in said mixture based on said measured mixture mass flow, said measured mixture density, and said first and second component values for their densities, and means to display said calculated amounts of said first and second components in said mixture.

14. The apparatus of claim 13, said display means comprising means to continuously display values corresponding to the volume contents of said first and of said second components in said mixture, and means to output signals from said display means usable externally of said apparatus.

15. The apparatus of claim 13, said calculating means comprising a micro-processor.

16. The apparatus of claim 13, wherein said mixture is crude oil, said first component is liquid petroleum, and said second component is water.

17. The apparatus of claim 13, wherein said apparatus is built into a portable device suitable for use at the wellhead of a hydrocarbon well.

18. The apparatus of claim 13, and means to adapt said apparatus for use at a production battery serving a plurality of hydrocarbon wells.

19. The apparatus of claim 13, means for measuring the temperature of said mixture, and means to obtain values for the thermal coefficients of expansion of said first and second components.

20. The apparatus of claim 19, wherein said calculating means includes means for first calculating the density of said first and second components at said measured temperature utilizing said measured temperature and said values for the densities and the thermal coefficients of expansion of said first and second components, means for calculating the percent of one of said first and second components in said mixture utilizing the measured mixture density and the previously calculated values for the densities of said first and second components, means for calculating the volume flow rate of the mixture utilizing said measured value of mixture mass flow and mixture density, means for calculating flow rates of said first and said second components utilizing the output of said last means of calculating the percent content of one of said components in said mixture and the mixture volume flow rate, and means for temperature correcting the first and second component calculated flow rates.

21. The apparatus of claim 20, wherein said thermal coefficients of expansion values are obtained at a reference temperature different from the temperature at which said mixture is measured, and means for correcting the percent volume contents of said first and second components to said reference temperature.

22. The apparatus of claim 13, wherein said mixture is crude oil, and means for time averaging the measured value of the density of said mixture.

23. The apparatus of claim 13, and alerting means, and means to connect said alerting means and said calculating means together so as to actuate said alerting means if the measured mixture density falls below some predetermined value.

24. The apparatus of claim 13, wherein said mixture is produced fluid from a hydrocarbon well, and separator means to separate any gas which may be present in said produced well fluid, said separator means being placed prior to the point where said mixture is flowed through said apparatus.

25. The apparatus of claim 24, wherein said separator means is a vertical three-phase separator.

26. The apparatus of claim 24, wherein said separator means comprises a vertical two-phase separator.

27. The apparatus of claim 24, wherein said separator means comprises a horizontal three-phase separator.

28. The apparatus of claim 24, wherein said separator means comprises a horizontal two-phase separator.

29. A method of determining the amounts of a first and of a second component in a flowing mixture comprising said first and second components, said first and second components being liquids and having different densities, comprising the steps of:
 (a) measuring the mass flow of said mixture;
 (b) determining the density of said mixture;
 (c) obtaining values for the densities of said first and second components;
 (d) calculating the amounts of said first and second components in said mixture based on said measured mixture mass flow rate, measured mixture density, and said first and second component obtained values for their said densities, said step of calculating amounts including the substeps of
  (i) calculating the density of said first and second components at said measured temperature, utilizing said measured temperature and said values for the densities and the thermal coefficients of expansion of said first and second components,
  (ii) calculating the percent of one of said first and second components in said mixture utilizing the measured mixture density and the previously calculated values for the densities of said first and second components,
  (iii) calculating the volume flow rate of the mixture utilizing said measured value of mixture mass flow and mixture density, the substeps of calculating amounts of said first and of said second components utilizing the output of said last mentioned substeps of calculating the percent of one of said components in said mixture, and the substep of calculating the mixture volume flow rate, and then the substep of temperature correcting the outputs of said last-mentioned two substeps of calculating the first and second component flow rates;
 (e) measuring the temperature of said mixture,
 (f) obtaining values for the thermal coefficients of expansion of said first and of said second components,
 (g) performing said calculating amounts step to include said measured mixture temperature and said thermal coefficients values to correct said calculated amounts for the difference in temperature between the measured temperature of said mixture and a predetermined reference temperature.

30. The method of claim 29, wherein said mixture is produced fluid from a well, said first component is liquid hydrocarbons, said second component is water, and further comprising the step of time averaging the measured value of the density of said mixture.

31. Apparatus for determining the amounts of a first and of a second component in a flowing mixture, said first and second components being normally liquids and having different densities comprising:
 (a) means to flow said mixture through said apparatus;
 (b) means to measure the mass flow, the density, and the temperature of said mixture;
 (c) means to obtain values for the densities of said first and of said second components;
 (d) means to calculate the amounts of said first and second components in said mixture based on said measured mixture mass flow, said measured mixture density, and said first and second component values for their densities, said calculating means further comprising:
  (i) means for first calculating the density of said first and second components at said measured temperature utilizing said measured temperature and said values for the densities and the thermal coefficients of expansion of said first and second components,
  (ii) means for calculating the percent of one of said first and second components on said mixture utilizing the measured mixture density and the previously calculated values for the densities of said first and second components, (iii) means for calculating the volume flow rate of the mixture utilizing said measured value of mixture mass flow and mixture density, (iv) means for calculating flow rates of said first and said second components utilizing the output of said last means of calculating the percent content of one of said components in said mixture and the mixture volume flow rate, and (v) means for temperature correcting the first and second component calculated flow rates, (e) means to display said calculated amounts of said first and second components in said mixture;

(f) means for measuring the temperature of said mixture;

(g) means to obtain values for the thermal coefficients of expansion of said first and second components.

32. The apparatus of claim 31, wherein said thermal coefficients of expansion values are obtained at a reference temperature different from the temperature at which said mixture is measured, and further comprising means for correcting the percent volume contents of said first and second components to said reference temperature.

* * * * *